United States Patent
Gutman et al.

(12)

(10) Patent No.: US 6,737,518 B1
(45) Date of Patent: May 18, 2004

(54) PROCESS FOR PREPARATION OF 4,5-EPOXYMORPHINAN-6-OXYGLUCURONIDES

(75) Inventors: Arie L. Gutman, Haifa (IL); Genadi Nisnevitch, Nesher (IL); Lev Yudovitch, Haifa (IL); Igor Rokhman, Kyriat Yam (IL)

(73) Assignee: CeNeS Limited, Cambridge (GB)

( * ) Notice: Subject to any disclaimer, the term of this patent is extended or adjusted under 35 U.S.C. 154(b) by 0 days.

(21) Appl. No.: 09/700,035

(22) PCT Filed: May 12, 1999

(86) PCT No.: PCT/GB99/01508

§ 371 (c)(1),
(2), (4) Date: May 18, 2001

(87) PCT Pub. No.: WO99/58545

PCT Pub. Date: Nov. 18, 1999

(30) Foreign Application Priority Data

May 13, 1998  (IL) ................................................. 124460
Jan. 15, 1999  (GB) ............................................... 9900832

(51) Int. Cl.$^7$ .......................... C07H 15/00; A61K 31/70
(52) U.S. Cl. .................... 536/18.5; 536/17.4; 536/18.1; 514/25
(58) Field of Search .............................. 536/17.4, 18.1, 536/18.5, 25

(56) References Cited

U.S. PATENT DOCUMENTS 5,621,087 A * 4/1997 Scheinmann et al. ....... 536/17.4

FOREIGN PATENT DOCUMENTS

WO   93/05057   3/1993
WO   WO 93 05057 A  * 3/1993 .......... C07H/17/00

OTHER PUBLICATIONS

Rukhman et al., Tetrahedron Letters, vol. 41, pp. 6889–6892, 2000.*
March, J., "Advanced Organic Chemistry", 4$^{th}$ Ed., pp. 260–263 (1992).
Berrang, B., et al., "Synthesis of Morphine–3, 6–di–β–D–glucuronide", Synthesis, pp. 1165–1168 (1997).
Brown, R., et al., "A Simple Synthesis of Morphine–3, 6–di–β–D–glucuronide", Tetrahedron 56, pp. 7591–7594 (2000).
Rukhman, I., et al. "Selective Synthesis of Both Isomers of Morphine 6–β–D–Glucuronide and Their Analogs", Tetrahedron 57, pp. 1083–1092 (2001).
"Synthesis of Ethylmorphine–6–glucuronide: a Metabolite of Ethylmorphine in Man," A. Bugge et al., Acta. Chem. Scand, vol. 49, No. 5, pp. 380–384, 1995.
"Synthesis and Analgesic Effect of Normorphine–3– and –6–glucuronides," Kazuta Oguri et al., Chem. Pharm. Bull., vol., 37, No. 4, 1989, pp. 955–957.
"Synthesis of O– and S–glucosides using glucosyl halides and zinc salts, " Kambadoor N. Gurudutt et al., Carbohydrate Research, vol. 258, 1996, pp. 159–165.

* cited by examiner

Primary Examiner—James O. Wilson
Assistant Examiner—Howard V. Owens, Jr.
(74) Attorney, Agent, or Firm—Finnegan, Henderson, Farabow, Garrett & Dunner, LLP

(57) ABSTRACT

Conjugation of 4,5-Epoxymorphinan-6-ols with Bromoglucuronides in the presence of Zinc containing compounds as activator under conditions capable of forming 4,5-Epoxymorphinan-6-oxyglucuronides is disclosed. This novel approach provides an efficient method for preparation of both anomers of 4,5-Epoxymorphinan-6-oxyglucuronides. The deprotected end products are useful as analgesic agents.

14 Claims, No Drawings

PROCESS FOR PREPARATION OF 4,5-EPOXYMORPHINAN-6-OXYGLUCURONIDES

BACKGROUND OF THE INVENTION

According to recent publications the morphine metabolite Morphine-6-β-D-glucuronide (M6G) [6] is a more effective and longer lasting analgesic drug than Morphine [5] with fewer side effects[1] and, therefore, there is much interest in using M6G, rather than Morphine, as a pain killing drug.[2]

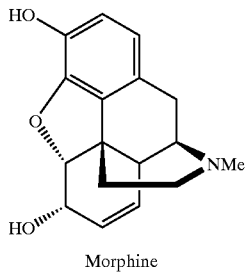

Morphine [5]

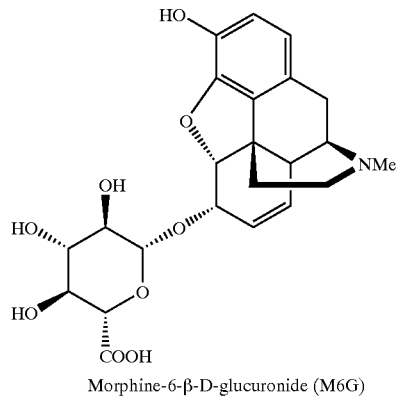

Morphine-6-β-D-glucuronide (M6G) [6]

The traditional approach to glycosylation of 4,5-Epoxymorphinan-6-ols explores Bromoglucuronides as glycoside donor and the Koenings-Knorr procedure for the activation of Bromoglucuronides (Berrang, B., et al., Synthesis, 1997, p. 1165 and references cited therein).

Another approach (Scheinmann, F. et. al., U.S. Pat. No. 5,621,087, see claim 1, 2, 5 and 6, abstract, examples, column 4, line 25–line 45) explores the use of Lewis acids (of the type $BF_3$ and TMSOTf) rather than heavy metals based Lewis acids (March, J., "Advanced Organic Chemistry", 4-th edition, A Whiley-Interscience publicaiton, pp. 260–3) for the activation of Bromoglucuronides.

Unfortunately, we did not succeed to obtain 4,5-Epoxymorphinan-6-oxyglucuronide from Bromoglucuronides using activators proposed in U.S. Pat. No. 5,621,087 and did not find such examples in the literature.

Unexpectedly we found that the O-glycosylation of 4,5-Epoxymorphinan-6-ols with Bromoglucuronides was accelerated by Zinc containing compounds to give 4,5-Epoxymorphinan-6-oxyglucuronides of formula [1] with high yield.

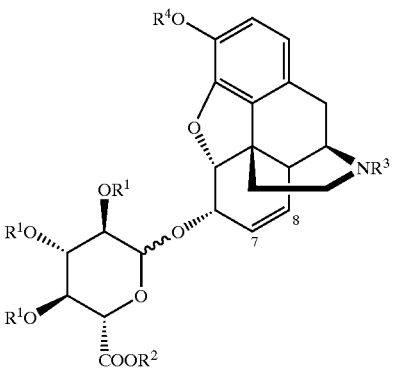

[1]

wherein:

position 7 and 8 can be olefin as shown or dihydro adduct;

$R^1$ are alkyl, haloalkyl, arylmethyl, acyl, alkoxycarbonyl, aralkoxycarbonyl, haloalkoxycarbonyl, vinyloxycarbonyl or allyloxycarbonyl, $R^2$ is alkyl, haloalkyl or aralkyl;

$R^3$ is alkyl, arylmethyl, allyl, cyclopropylmethyl, cyclobutylmethyl, acyl, alkoxycarbonyl, aralkoxycarbonyl, haloalkoxycarbonyl, vinyloxycarbonyl, allyloxycarbonyl or hydrogen;

$R^4$ is alkyl, haloalkyl, arylmethyl, 2-(4-morpholinyl)ethyl, acyl, alkoxycarbonyl, aralkoxycarbonyl, haloalkoxycarbonyl, vinyloxycarbonyl or allyloxycarbonyl.

We also found that the α and β anomeric selectivity of the conjugation product can be controlled by using different O-protecting groups in aglycon and in Bromoglucuronide as well as by varying the ratio between 4,5-Epoxymorphinan-6-ols and Zinc containing compounds.

It is important to note that only the β-anomer of 4,5-Epoxymorphinan-6-oxyglucuronides was obtained according to Koenings-Knorr procedure and U.S. Pat. No. 5,621,087 procedure (but with other than a Bromoglucuronide glycoside donor).

All of the previously disclosed methods have serious drawbacks for producing material to be used as a pharmaceutical drug. A desirable goal, met by the present invention, has been to devise a synthetic procedure without using commercially inaccessible and expensive reagents, and which cleanly produces the desired 4,5-Epoxymorphinan-6-oxyglucuronides, avoiding tedious and expensive purification steps.

SUMMARY OF THE INVENTION

The present invention provides a commercially acceptable process for conjugation of 4,5-Epoxymorphinan-6-ols of formula [3] with Bromoglucuronides of formula [2] in the presence of Zinc containing compounds under conditions capable of forming 4,5-Epoxymorphinan-6-oxyglucuronides [1].

[2]

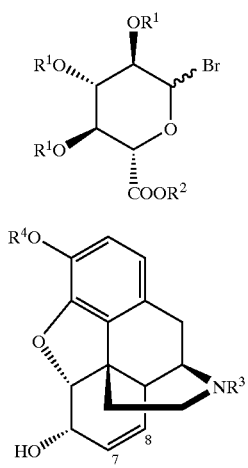

[3]

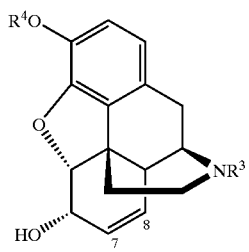

wherein
position 7 and 8 can be olefin as shown or dihydro adduct;
$R^1$, $R^2$, $R^3$, and $R^4$, are as defined above.

This novel approach was used for the preparation of the known analgesic agent Morphine-6-β-glucuronide [4] and of its α-anomer.

[4]

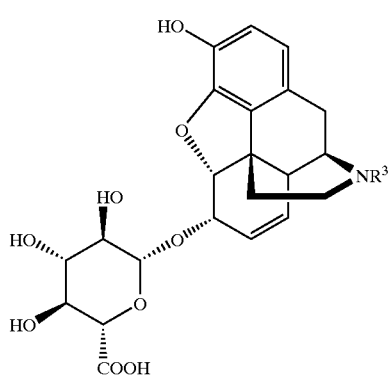

Other features and advantages will be apparent from the specification and claims.

DETAILED DESCRIPTION OF THE INVENTION

The present invention is related to a novel process for conjugation of 4,5-Epoxymorphinan-6-ols with Bromoglucuronides.

Particularly, the present invention relates to the use of Zinc containing compounds for the activation of Bromoglucuronides in the O-glycosylation reaction of 4,5-Epoxymorphinan-6-ols.

This novel approach has the following advantages:
Zinc containing compounds as activating reagents of Bromoglucuronides are inexpensive and commercially available.
Use of different O-protecting, groups in the aglycon and in the Bromoglucuronide as well as different ratio of 4,5-Epoxymorphinan-6-ols and Zinc containing compounds enable to obtain high anomeric selectivity and produce at will with a high degree of preference either the α or the β anomer.

Although any 4,5-Epoxymorphinan-6-ols are suitable for this O-glycosylation, preferably, compounds of formula [3] are used

[3]

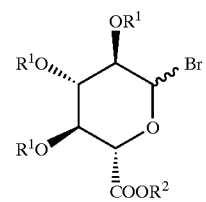

wherein
position 7 and 8 can be olefin as shown or dihydro adduct;
$R^3$ and $R^4$ are as previously defined.

More preferably, said 4,5-Epoxymorphinan-6-ols are selected from 3-O-Acylmorphine, 3-O-Acylnormorphine, 3-O-Acylnalbuphine, 3-O-Acylnalorphine, 3-O-Acyldihydromorphine, 3-O-Benzylmorphine, 3-O-Benzyldihydromorphine, N,$O^3$-Dibenzylnormorphine, Codeine, Ethylmorphine, Dihydrocodeine, Pholcodine, 3-O-Alkoxycarbonylmorphine, 3-O-Benzyloxycarbonylmorphine, N,$O^3$-Bis(benzyloxycarbonyl)normorphine.

Although any Bromoglucuronide may be used, it is preferred that compounds of formula [2] are used.

[2]

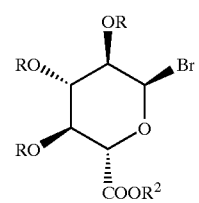

wherein
$R^1$ and $R^2$ are as previously defined.

More preferably the Bromoglucuronides of the present invention are selected from the compounds of formula [2a].

[2a]

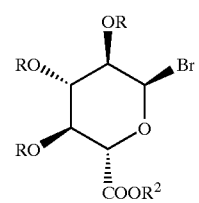

wherein
R are acyl, alkoxycarbonyl, aralkoxycarbonyl, haloalkoxycarbonyl, vinyloxycarbonyl, allyloxycarbonyl;
$R^2$ is as previously defined.

Most preferably Bromoglucuronides of formula [2b] are used.

[2b]

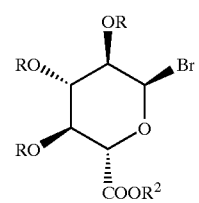

wherein
R are as previously defined.

Although any Zinc containing compound suitable as activating reagents for this O-glycosylation can be used, preferably, Zinc Bromide is used.

It is preferred that about 0.01 equivalents to about 4 equivalents and especially preferred that about 0.5 equivalents to about 2 equivalents of Zinc containing compound is used.

Preferably about 1 equivalent to about 2 equivalents of the Bromoglucuronide [2] is used. It is specially preferred that about 1 equivalent to about 1.5 equivalents of Bromoglucuronide [2] is used. The said 4,5-Epoxymorphinan-6-ol [3] may be used as an individual compound or alternatively as corresponding salts thereof or complexes. Especially preferred is the use of said Zinc containing salt or complexes of [3] without using additional Zinc containing compounds as promoter for said coupling. It is preferred that the said complexes may be prepared in situ.

It may be also preferred to conduct the said Zinc activated O-glycosylation in the presence of additives to buffer or to promote the said Zinc containing compounds. The above additives may be selected from molecular sieves, tertiary amines, tetraalkylureas, organic and inorganic acids and salts.

Any reaction-inert solvent may be used. As used above and elsewhere herein, the expression "reaction-inert solvent" refers to a solvent which does not react or decompose with starting materials, reagents, intermediates or products in a manner which adversely affects the yield of the desired product. In general, the solvent can comprise a single entity, or contain multiple components. Preferably the sovent is a non-protic reaction inert solvent and it is especially preferred that the solvent is Dichloromethane because of the exellent stereoselectivity it provides. Another solvent may be Chloroform or Dichloroethane.

Any environment or conditions (e.g. temperature, time, solvent) suitable for (i.e., capable of) forming the desired 4,5-Epoxymorphinane-6-oxyglucuronides may be used. However, it is preferred that the reaction occurs at a temperature of about −20° C. to about 100° C. and preferably from about 40° C. to 65° C. Below about −20° C. the reaction can be slow and above about 100° C. undesired side reactions (e.g. anomerisation) can occur. This reaction is conveniently carried out at about 0.5 to about 3 atmospheres, however, the high pressures are espesially preferred for the said coupling.

The present invention could be used as a general method to produce a large number of new compounds. As a result of the said coupling also the salts and complexes of 4,5-epoxymorphinan-6-oxyglucuronides [1] could be obtained in a convenient way.

This invention makes a significant advance in the field of 4,5-Epoxymorphinan-6-oxyglucosides by providing efficient methods of preparing both anomers of 4,5-Epoxymorphinan-6-oxyglucuronides. The deprotected end products are useful as analgesic agents.

It should be understood that the invention is not limited to the particular embodiments shown and described herein, but that various changes and modifications may be made without departing from the spirit and scope of this novel concept as defined by the following claims.

EXAMPLES

Example 1

Preparation of Codeine-β-glucuronide [4a]

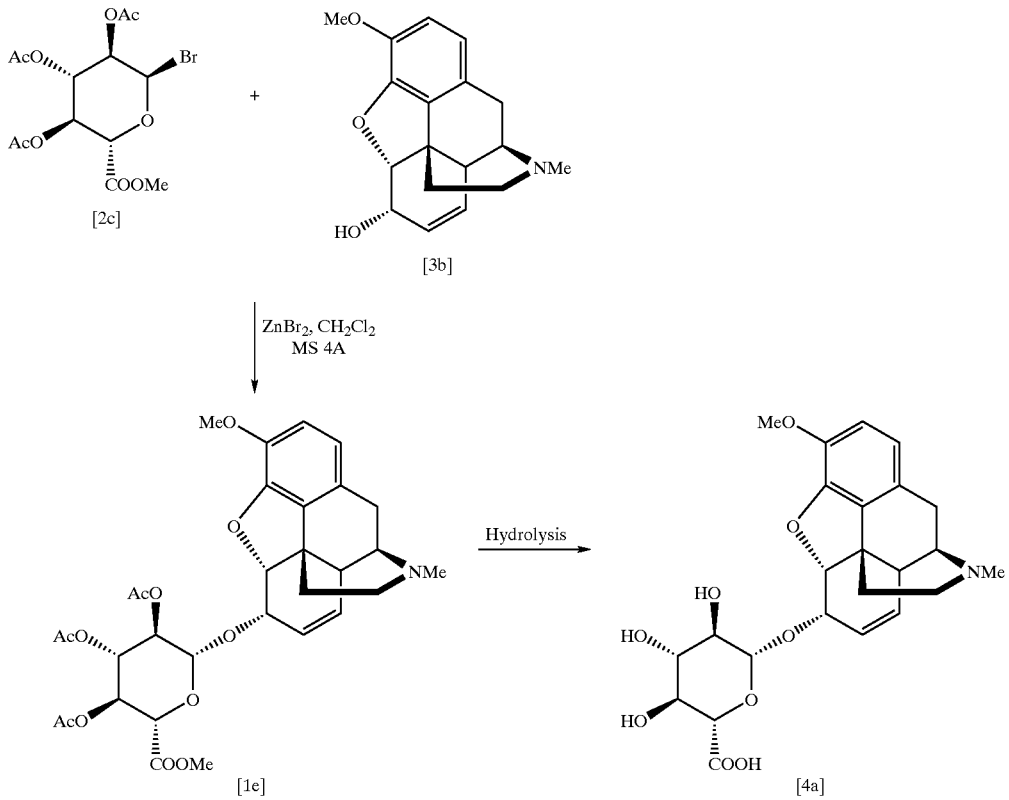

1.1 Preparation of Methyl (3-O-Methylmorphin-6-yl-2',3',4'-tri-O-acetyl-β-D-glucopyranosid)uronate [1e]

A mixture of Methyl acetobromo-α-D-glucuronate [2c] (0.20 g), Codeine [3b] (0.10 g), 3 Å Molecular Sieves (0.3 g) and Dichloromethane (10 mL) was stirred at room temperature for 5 hours. Anhydrous Zinc Bromide (0.08 g) was added in one portion and the resulting mixture was refluxed for 48 hours. Dichloromethane (20 mL) and Sodium Hydrogencarbonate saturated aqueous solution (10 mL) were added to the cooled reaction mixture. After stirring for 30 min the organic layer was separated and washed with Sodium Hydrogencarbonate saturated aqueous solution and Water. The aqueous layers were combined and washed with Dichloromethane (20 mL) The combined organic layers were dried over anhydrous Sodium Sulfate, filtered and evaporated under reduced pressure. After purification of the residue the desired product was obtained in the yield of 58% (0.12 g). Its structure was confirmed by $^1$H NMR (CDCl$_3$)

1.2 Hydrolysis of Compound [1e]

Hydrolysis of compound [1e] was carried out according to the known procedure (Carrupt, P.-A. et al., J. Med. Chem., 1991, v. 34, 1272). Codeine-β-glucuronide was obtained with 50% yield. Its structure was confirmed by $^1$H NMR (D$_2$O), $^{13}$C NMR, HR–MS.

Example 2

Preparation of Morphine-6-β-glucuronide [M6G] [4]

2.1 Preparation of Methyl (3-O-methoxycarbonylmorphin-6-yl-2',3',4'-tri-O-acetyl-β-D-glucopyranosid)uronate [1f]

A mixture of Methyl acetobromo-α-D-glucuronate [2c], (39.7 g, 100 mmol), 3-O-Methoxycarbonylmorphine [3c] (22.8 g, 66.5 mmol) 3 Å Molecular Sieves (50.0 g) and Chloroform (300 mL) was stirred at room temperature for 1 hour. Anhydrous Zinc Bromide (16.1 g, 71.4 mmol) was added in one portion and the resulting mixture was stirred at 50–55° C. for 60 hours under Argon. Sodium Hydrogencarbonate saturated aqueous solution (200 mL) was added to the cooled to room temperature reaction mixture and the stirring was continued for additional 30 min. The organic layer was separated, washed with water, dried over anhydrous Sodium Sulfate, filtered through a short Silica gel column and evaporated under reduced pressure to give 35.0 g (80%) of the crude product. After crystallisation from iso-Propanol 20.3 g (46.4% yield) of Methyl (3-O-methoxycarbonylmorphin-6-yl-2',3',4'-tri-O-acethyl-β-D-glucopyranosid)uronate [1f] was obtained. Its structure was confirmed by $^1$H NMR (CDCl$_3$).

2.2 Hydrolysis of Compound [1f]

Hydrolysis of compound [1f] was carried out according to known procedure (Carrupt, P.-A. et al., J. Med. Chem., 1991, v. 34, 1272) and gave M6G [4] with 56% yield. Its structure was confirmed by $^1$H NMR (D$_2$O), $^{13}$C NMR.

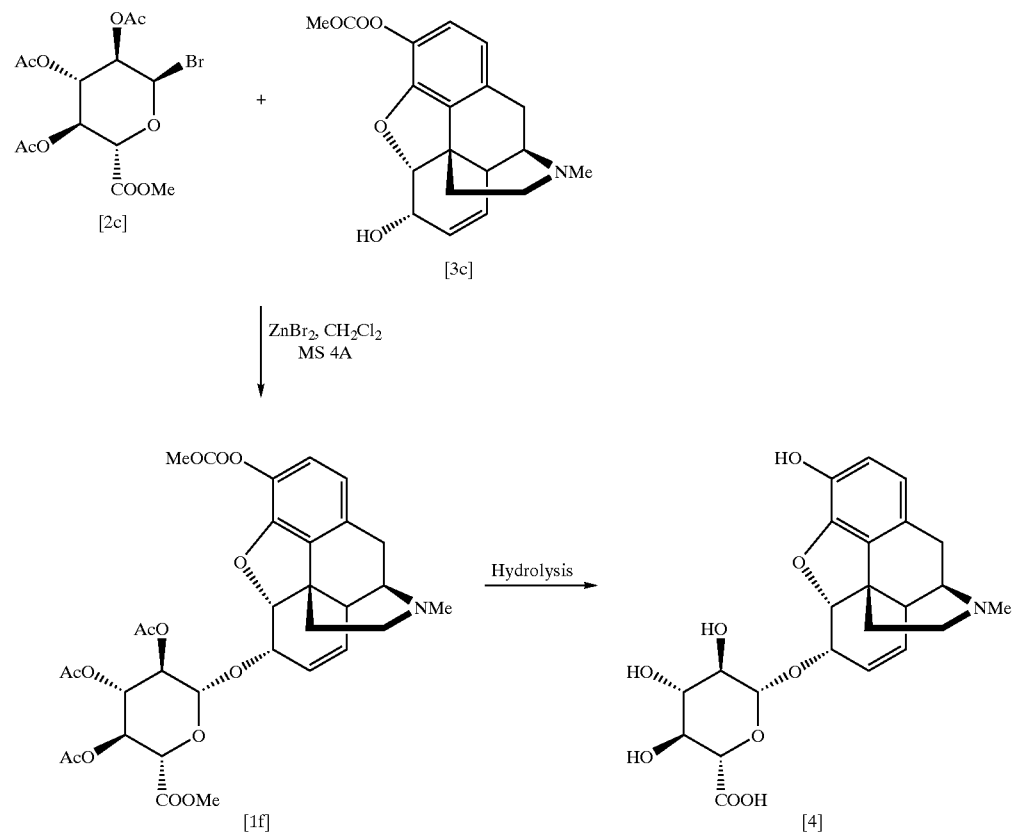

Example 3

Preparation of Morphine-6-α-glucuronide [4b]

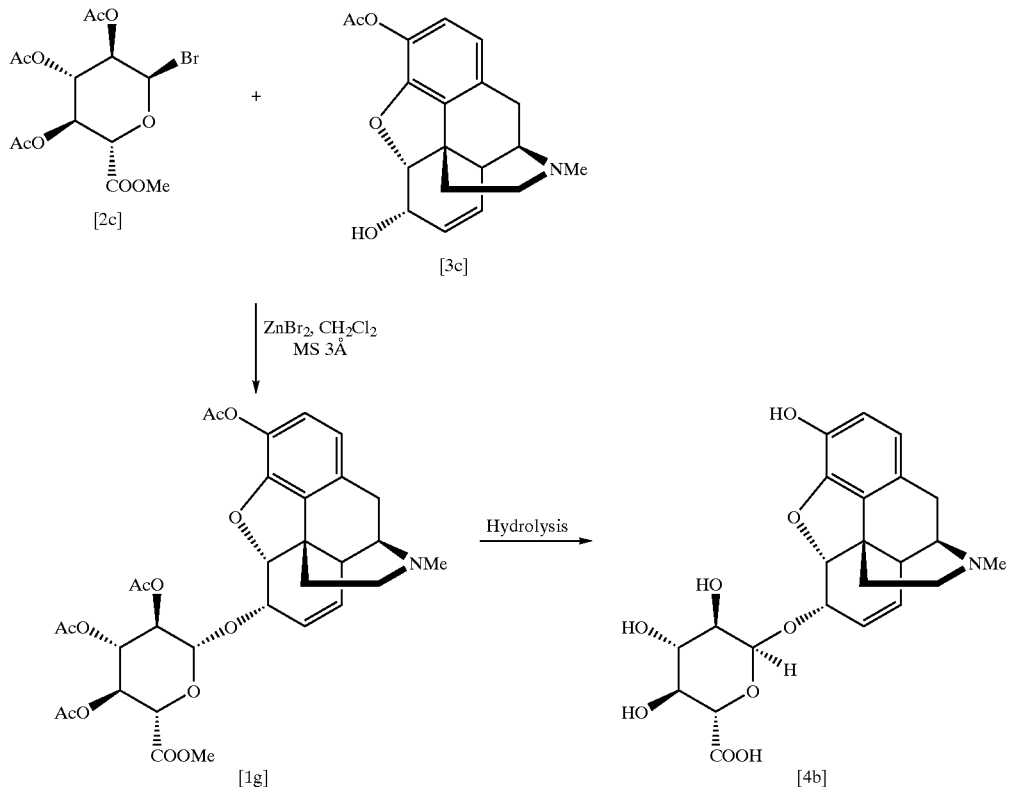

3.1 Preparation of Methyl (3-O-acetylmorphin-6-yl-2',3',4'-tri-O-acetyl-α/β-D-glucopyranosid)uronate [1g]

A mixture of Methyl acetobromo-α-D-glucuronate [2c] (6.0 g, 15 mmol), 3-O-Acetylmorphine [3c] (3.23 g, 10 mmol) and 3 Å Molecular Sieves (9.0 g) and Dichloromethane (50 mL) was stirred at room temperature for 5 hours. Anhydrous Zinc Bromide (4.50 g, 20 mmol) was added in one portion and the resulting mixture was refluxed for 48 hours. Solution of Sodium hydrogencarbonate (8.0 g) in 80 mL water and Dichloromethane (80 mL) were added to the cold solution. After stirring for 30 min the organic layer was separated and the aqueous layer was washed with Dichloromethane. The combined organic solution was washed with water, dried over anhydrous Sodium Sulfate, filtered and evaporated under reduced pressure. The residue was purified on a short Silica gel column (Dichloromethane→Dichloromethane/Methanol 30:1 v/v) and after concentration under reduced pressure 5.7 g of yellowish powder of the desired Methyl(3-O-acetylmorphin-6-yl-2',3',4'-tri-O-acetyl-D-glucopyranosid)uronate [1g] (α/β 6:1 mixture according to $^1$H NMR spectra) (91% yield) was obtained.

3.2 Hydrolysis of Compound [1g]

Sodium Hydroxide (0.40 g, 10.0 mmol) solution in 7.5 mL water was added to a stirred solution of Methyl (3-O-acetylmorphin-6-yl-2',3',4'-Tri-O-acetyl-α/β-D-glucopyranosid)uronate (1.6 g, 2.0 mmol) in 30 mL Methanol and the mixture was stirred overnight at room temperature. The solution was then acidified with glacial Acetic acid (5.25 g, 87.3 mmol) to pH 5.5. The solution was cooled to 0° C., Ethanol (20 mL) was added and the obtained mixture was stirred for 1.5 hours. The white precipitate formed under these conditions was filtered off and washed with Ethanol (2 mL). After drying under reduced pressure at 80° C. 0.63 g (62% yield) of Morphine-6-α-glucuronide [4b] was obtained. Its structure was confirmed by $^1$H NMR ($D_2O$), $^{13}$C NMR, HR–MS.

Example 4–20

Preparation of Compound of Formula [1b]

The syntheses are described by the following Scheme.

The procedures set forth in Example 3 were followed with the exceptions apparent from Table 1. Ratio β/α was determined according to $^1$H NMR and/or HPLC.

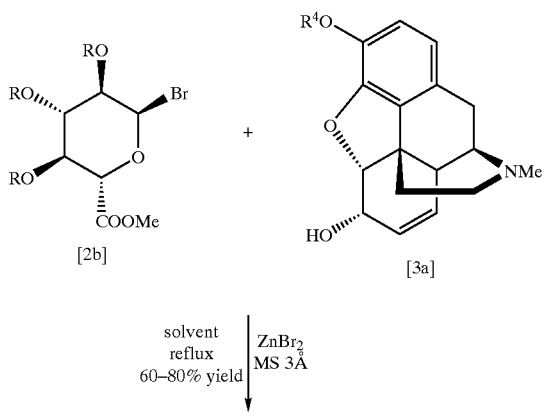

-continued

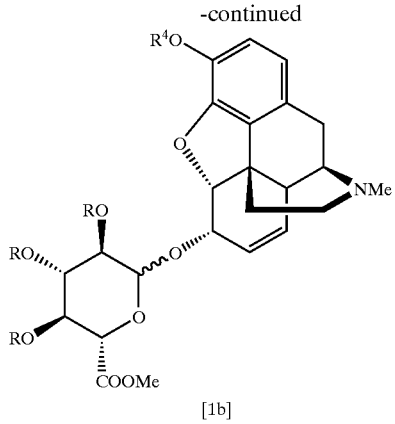

[1b]

The procedures set forth in Example 3 were followed with the exceptions apparent from Table 1. Ratio β/α was determined according to ¹H NMR and/or HPLC.

TABLE 1

| Ex. No. | R⁴ | R | ZnBr₂/[3a] | Solv. | β/α |
|---|---|---|---|---|---|
| 4 | Ac | Ac | 0.8 | CH₂Cl₂ | 10:1 |
| 5 | Ac | Ac | 0.9 | CH₂Cl₂ | 6:1 |
| 6 | Ac | Ac | 1.0 | CH₂Cl₂ | 2:1 |
| 7 | Ac | Ac | 1.2 | CH₂Cl₂ | 1:2 |
| 8 | Ac | Ac | 1.5 | CH₂Cl₂ | 1:4 |
| 9 | Ac | Ac | >1.5 | CH₂Cl₂ | 1:6 |
| 10 | Ac | i-Bu | 0.90 | CH₂Cl₂ | 2:1 |
| 11 | Ac | i-Bu | 1.2 | CH₂Cl₂ | 1:1 |
| 12 | i-Bu | i-Bu | 0.85 | CH₂Cl₂ | 3.5:1 |
| 13 | i-Bu | i-Bu | 1.0 | CH₂Cl₂ | 2:1 |
| 14 | Bz | Ac | 1.0 | CH₂Cl₂ | 2:1 |
| 15 | Bz | i-Bu | 0.9 | CH₂Cl₂ | 29:1 |
| 16 | Bz | i-Bu | 1.5 | CH₂Cl₂ | 6:1 |
| 17 | Bz | Bz | 1.0 | CH₂Cl₂ | 10:1 |
| 18 | MeOCO | Ac | 1.0 | CHCl₃ | 6:1 |
| 19 | MeOCO | Ac | 1.4 | CH₂Cl₂ | 5:1 |
| 20 | Me | Ac | 1.1 | CH₂Cl₂ | >99:1 |

Example 21

Preparation of Methyl (3-O-Acetylmorphin-6-yl-2', 3',4'-Tri-O-acetyl-β-D-glucopyranosid)uronate of Formula [8]

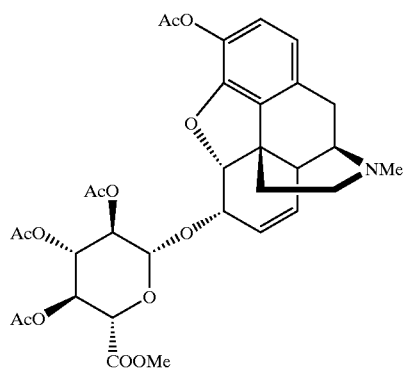

[8]

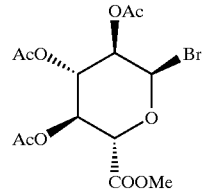

[9]

A suspension of 6.00 g of Methyl Tri-O-acetyl-1-α-bromo-1-deoxy-D-glucopyranuronate of formula [9], 3.23 g of freshly prepared, vacuum-dried 3-O-Acetylmorphine⁶ and 9.00 g of 3 Å Molecular Sieves in CH₂Cl₂ was stirred at room temperature for 5 hours. Anhydrous Zinc Bromide, 2.20 g was added in one portion and the resulting mixture was refluxed for 24 hours. Then an additional 0.30 g of anhydrous Zinc Bromide was added and the mixture was refluxed for additional 24 hours. After this period, the red solution was cooled to room temperature and the mixture of Methylene Chloride (150 mL) and Sodium Hydrogen carbonate saturated aqueous solution (80 mL) was added to the reaction mixture. After stirring for 30 min. the organic layer was separated and washed consequently with Sodium Hydrogen carbonate saturated aqueous solution and Water. The combined aqueous layers were washed with Methylene Chloride. The combined organic layers were dried over Sodium Sulphate anhydrous, filtered and evaporated under reduced pressure. After purification of the residue the desired product was obtained in the yield of 91% (5.7 g).

References

1. Osborne, R., et al., Br. J. Clin. Pharm. 1992, v. 34, 130
2. Frances, B., et al., J. Pharm. Exp. Ther., 1992, v. 262, 25

What is claimed is:

1. A process for the synthesis of a protected 4,5-Epoxymorphinan-6-oxyglucuronide of formula [1] or a salt or complex thereof

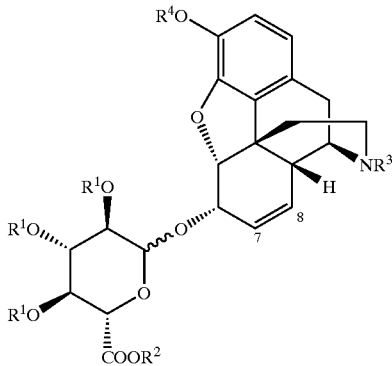

[1]

wherein:
position 7 and 8 are olefin as shown or dihydro adduct;
$R^1$ is acyl;
$R^2$ is methyl;
$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl or allyloxycarbonyl;
$R^4$ is alkyl, arylmethyl, acyl, alkoxycarbonyl, aralkoxycarbonyl, haloalkoxycarbonyl, vinyloxycarbonyl or allyloxycarbonyl;

comprising reaction of a Bromoglucuronide of the formula [2]

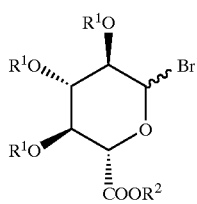
[2]

wherein $R^1$ and $R^2$ are as previously defined;

with a 4,5-Epoxymorphinan-6-ol of the formula [3] or a salt or complex thereof

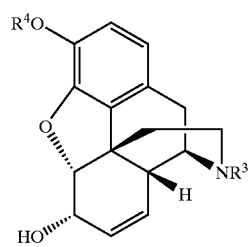
[3]

wherein $R^3$ and $R^4$ are as previously defined; and position 7 and 8 are olefin as shown or dihydro adduct;

in the presence of a Zinc bromide under conditions capable of forming said protected 4,5-Epoxymorphinan-6-oxyglucuronide [1] or a salt or complex thereof.

2. A process according to claim 1 wherein said 4,5-Epoxymorphinan-6-ol is selected from the compounds of the formula [3a]

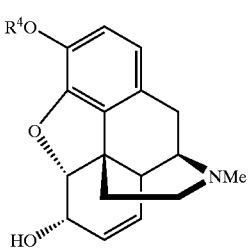
[3a]

wherein $R^4$ is as previously defined.

3. A process according to claim 1 wherein said 4,5-Epoxymorphinan-6-ol is selected from 3-O-Acylmorphine, 3-O-Acylnormorphine, 3-O-Acylnalbuphine, 3-O-Acylnalorphine, 3-O-Acyldihydromorphine, 3-O-Benzylmorphine, 3-O-Benzyldihydromorphine, N,O³-Dibenzylnormorphine, Codeine, Ethylmorphine, Dihydrocodeine, Pholcodine, 3-O-Alkoxycarbonylmorphine, 3-O-Benzyloxycarbonylmorphine, N,O³-Bis(benzyloxycarbonyl)normorphine.

4. A process according to claim 1 wherein said Bromoglucuronide is selected from compounds of formula [2a]

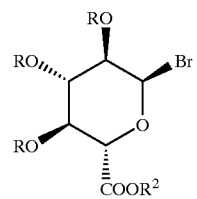
[2a]

wherein

R is acyl; and $R^2$ is as previously defined.

5. A process as recited in claim 1 wherein said protected 4,5-Epoxymorphinan-6-oxyglucuronide is an N-Methyl-4,5epoxymorphinan-6-oxyglucuronide of formula [Ia] or derivative thereof

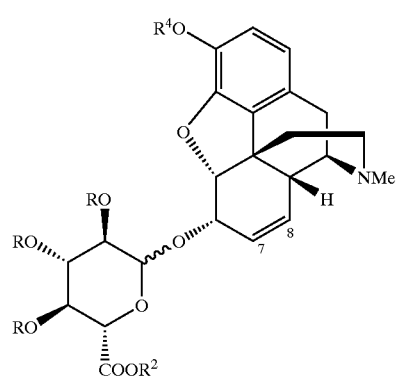
[1a]

wherein:

position 7 and 8 can be olefin as shown or dihydro adduct;

R is acyl; and $R^2$ and $R^4$ are as previously defined.

6. A process as recited in claim 1 wherein $R^3$ is methyl.

7. A process as recited in claim 1 wherein the said reaction occurs in the presence of molecular sieves.

8. A process as recited in claim 1 wherein the reaction occurs in a non-protic reaction inert solvent.

9. A process as recited in claim 8 wherein the inert solvent is selected from Chloroform, Dichloromethane or Dichloroethane.

10. A process for the preparation of a protected 4,5-Epoxymorphinan-6-oxyglucuronide of a general formula [1] or a salt or complex thereof

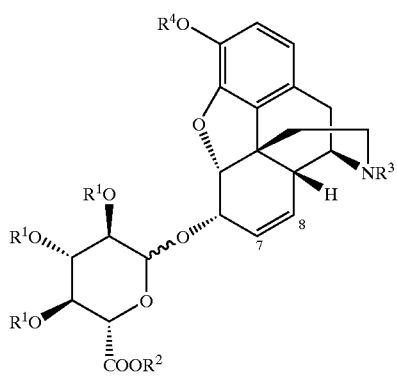

wherein
position 7 and 8 are olefin as shown or dihydro adduct;
$R^1$ is acyl;
$R^2$ is methyl;
$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl or allyloxycarbonyl;
$R^4$ is alkyl, arylmethyl, acyl, alkoxycarbonyl, aralkoxycarbonyl, haloalkoxycarbonyl, vinyloxycarbonyl or allyloxycarbonyl;
comprising reacting a Bromglucuronide of the formula [2]

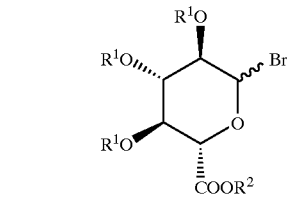

wherein:
$R^1$ and $R^2$ are as previously defined;
with a Zinc complex of general formula [3b]

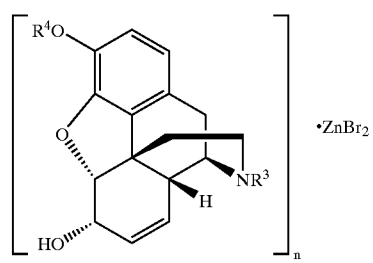

wherein:
position 7 and 8 are olefin as shown or dihydro adduct;
$R^3$ and $R^4$ are as previously defined; and
n is 0.5 to 2
under conditions capable of forming said protected 4,5-Epoxymorphinan-6-oxyglucuronide of a general formula [1] or a salt or complex thereof.

11. A process for the synthesis of a protected 4,5-Epoxymorphinan-6-oxyglucuronide of formula [1] or a salt or complex thereof

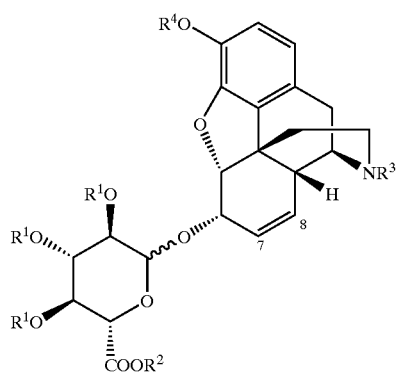

wherein:
position 7 and 8 are olefin as shown or dihydro adduct;
$R^1$ is acyl;
$R^2$ is methyl;
$R^3$ is alkyl, arylmethyl, allyl, cyclopropylmethyl, cyclobutylmethyl, hydrogen, acyl, alkoxycarbonyl, aralkoxycarbonyl, haloalkoxycarbonyl, vinyloxycarbonyl or allyloxycarbonyl;
$R^4$ is alkyl, arylmethyl, acyl, alkoxycarbonyl, aralkoxycarbonyl, haloalkoxycarbonyl, vinyloxycarbonyl or allyloxycarbonyl;
comprising reacting a Bromglucuronide of the formula [2]

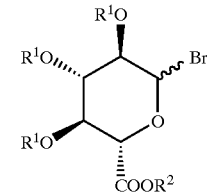

wherein
$R^1$ and $R^2$ are as previously defined;
with complex of the formula [3b]

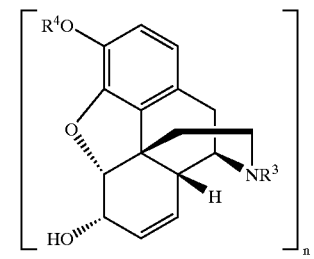

wherein:
$R^3$ and $R^4$ are as previously defined;
n is 0.5 to 2; and
position 7 and 8 are olefin as shown or dihydro adduct;
under conditions capable of forming said protected 4,5-Epoxymorphinan-6-oxyglucuronide [1] or a salt or complex thereof.

12. A compound having the following formula:

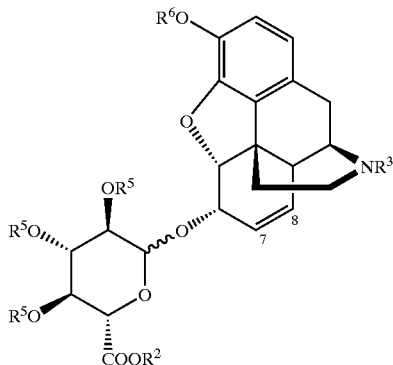

[1c]

wherein:
  position 7 and 8 is olefin as shown or dihydro adduct;
  $R^2$ is methyl; and
  $R^3$ is alkyl, arylmethyl, allyl, cyclopropylmethyl, cyclobutylmethyl, hydrogen, or acyl;
  $R^6$ is selected from alkoxycarbonyl, aralkoxycarbonyl, haloalkoxycarbonyl, vinyloxycarbonyl or allyloxycarbonyl; and
  $R^5$ is acyl.

13. A compound of formula [Ic] according to claim 12 wherein $R^3$ is Me.

14. A process for synthesizing M6G comprising: synthesizing a protected 4,5-Epoxymorphinan-6-oxyglucuronide according to any one of claims 1–4, 5, 6, 8, 9 and 11; and hydrolyzing the protected 4,5-Epoxymorphinan-6-oxyglucuronide to form M6G.

* * * * *